(12) United States Patent
Matsuo et al.

(10) Patent No.: US 6,510,728 B2
(45) Date of Patent: Jan. 28, 2003

(54) GAS SENSOR INCLUDING INORGANIC POWDER FILLING GAP BETWEEN MEASURING ELEMENT AND METALLIC SHELL

(75) Inventors: Kouji Matsuo, Aichi (JP); Satoshi Ishikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/769,273

(22) Filed: Jan. 26, 2001

(65) Prior Publication Data
US 2001/0023611 A1 Sep. 27, 2001

(30) Foreign Application Priority Data
Jan. 27, 2000 (JP) ........................................ 2000-018317

(51) Int. Cl.$^7$ ............................. G01N 27/04; G01N 7/00
(52) U.S. Cl. ..................... 73/31.05; 73/23.2; 204/424
(58) Field of Search ................... 73/23.2, 31.05; 204/424

(56) References Cited

U.S. PATENT DOCUMENTS

| | | | | |
|---|---|---|---|---|
| 4,088,555 A | * | 5/1978 | Kita et al. | .......... 204/428 |
| 4,591,423 A | * | 5/1986 | Kato et al. | .......... 204/426 |
| 4,986,892 A | * | 1/1991 | Kato et al. | |
| 5,874,663 A | | 2/1999 | Fukaya et al. | .......... 73/23.32 |

FOREIGN PATENT DOCUMENTS

| | | |
|---|---|---|
| JP | 58-6455 | 1/1983 |
| JP | 9-127047 | 5/1997 |
| JP | 9-127050 | 5/1997 |
| JP | 9-196885 | 7/1997 |
| JP | 11-295263 | 10/1999 |

OTHER PUBLICATIONS

Aglietti, E. F. et al. Material Res. Bull. 1992 (no month). vol. 27, pp. 1205–1216. "Physicohemical and thermal properties of mechanochemically activated talc".*
Filio, J. M. et al. Int. J. of The Soc. of Mat. Eng. for Resources. 1993 (no month). vol. 1, No. 1, pp. 140–147. "Effect of dry grinding on the structures and physical properties of pyrophyllite and talc by a planetary ball mill".*
Sanchez–Soto, P. J. et al. Applied Clay Science 1997 (no month), vol. 12, pp. 297–312. "Talc from Puebla de Lillo, Spain. II. Effect of dry grinding on particle size and shape".*
USGS Fact Sheet FS–065–00, Sep. 2000. "U.S. Talc—Baby Powder and Much More".*

* cited by examiner

Primary Examiner—Hezron Williams
Assistant Examiner—Michael Cygan
(74) Attorney, Agent, or Firm—Sughrue Mion, PLLC

(57) ABSTRACT

A gas sensor including a metallic shell (1) and an element (2), which is disposed in a hollow portion formed in the metallic shell (1). An inorganic powder (4) is filled into a gap between the element (2) and the metallic shell (1) to thereby hermetically seal the element (2) and the metallic shell (1) against each other. By using an inorganic powder (4) which does not have an exothermic peak within a temperature range up to 700° C. when subjected to differential thermal analysis, gastightness maintained at the gap portion between the element (2) and the metallic shell (1) is not impaired even in a working environment of 600° C. or higher. Talc powder composed of $SiO_2$ and MgO can be used as the inorganic powder (4). However, a binder, such as water glass, is not added to the inorganic powder (4) in order to prevent the inorganic powder (4) from having an exothermic peak within a temperature range up to 700° C., which peak would otherwise appear when the talc powder is subjected to thermal analysis. In order to attain good formability, a material stone of talc is pulverized into particles having a particle size of 400 $\mu$m to 600 $\mu$m and the particles are used as the inorganic powder (4).

13 Claims, 3 Drawing Sheets

GAS SENSOR INCLUDING INORGANIC POWDER FILLING GAP BETWEEN MEASURING ELEMENT AND METALLIC SHELL

BACKGROUND OF THE INVENTION

1. Field of the Invention

The present invention relates to a gas sensor for detecting the concentration of a component gas contained in a gas to be measured, such as exhaust gas from an internal combustion engine.

2. Description of the Related Art

Conventionally, gas sensors are used for measuring the concentration of a component gas contained in a gas to be measured. For example, Japanese Patent Application Laid-Open (kokai) Nos. 9-196885 and 11-295263 disclose oxygen sensors having a cylindrical element. Further, another oxygen sensor having a cylindrical element is disclosed in Japanese Patent Application No. 11-228322. Meanwhile, Japanese Patent Application Laid-Open (kokai) No. 9-127050 discloses an oxygen sensor having a strip-shaped element.

In order to dispose an element for detecting a component gas in a path along which a gas to be measured flows, the above-mentioned conventional gas sensors are configured, for example, as shown in FIG. 1. Specifically, the element is disposed in a hollow portion extending through a metallic shell, and an inorganic powder, such as talc or a ceramic powder, is filled into a gap between the metallic shell and the element so as to hermetically seal the metallic shell and the element against each other. Particularly, when high gastightness must be established, an upper portion of the metallic shell is caulked so as to compress the filling inorganic powder from above to thereby enhance gastightness of the inorganic powder.

A conventional process for filling the inorganic powder into the gap between the element and the metallic shell will next be described with reference to FIG. 1. First, talc having a grain size of 5 $\mu$m to 50 $\mu$m is prepared. Water glass is mixed into the talc in an amount of 4 parts by weight per 100 parts by weight of talc. The resultant mixed powder is formed under pressure into a sheet. The thus-formed sheet is pulverized and sieved to obtain secondary particles having a particle size of 300 $\mu$m to 800 $\mu$m. The thus-obtained powder is placed into a die, and then compacted into the form of a ring. The ring-shaped compact is inserted into the gap between the element and the metallic shell. The inserted compact is crushed from above by means of a hydraulic press to thereby fill the gap with the inorganic powder. Then, a sleeve of alumina ceramic is inserted from above and placed onto the inorganic powder. An upper portion of the metallic shell is caulked so as to compress the inorganic powder via the sleeve, to thereby enhance gastightness of the inorganic powder.

The reason why water glass is mixed into the inorganic powder in the above-described process is that compressibility of the inorganic powder can be improved by the mixed water glass. As described in Japanese Patent Application No. 11-123122, when the water glass content is set to 2 to 7 parts by weight per 100 parts by weight of the organic powder, the resulting mixed powder exhibits improved workability when compacting into a ring. Also, when the ring is built into a gas sensor, the ring can be compressed at a high compression rate, so that the gas sensor thus assembled has a high degree of gastightness.

However, studies carried out by the present inventors reveal that when talc containing water glass is used as described above, sufficient gastightness cannot be maintained for a long period of time in an environment of 600° C. or higher. That is, when water glass is contained in talc, the properties of the water glass change at temperatures higher than 600° C., resulting in grain growth of the talc. Thus, high powder fluidity peculiar to talc is lost, resulting in impaired gastightness.

SUMMARY OF THE INVENTION

An object of the present invention is to solve the above-mentioned problems in a conventional gas sensor and to provide a gas sensor, in which an inorganic powder is filled into a gap between a metallic shell and a sensing element disposed in the metallic shell in order to establish a hermetic seal between the sensing element and the metallic shell, and which can maintain the established hermetic seal even when the gas sensor is used in an environment of 600° C. or higher.

The above object, based on studies which the present inventors conducted on properties of an inorganic powder, has been achieved by providing a gas sensor comprising an inorganic powder which does not have an exothermic or endothermic peak within a temperature range up to 700° C. when the inorganic powder is subjected to differential thermal analysis. If the inorganic powder does not produce an exothermic or endothermic peak when subjected to differential thermal analysis within a temperature range up to 700° C., grains of the inorganic powder do not grow within a temperature range up to 700° C. Thus, the gas sensor can maintain sufficient gastightness even in a working environment of 600° C. or higher.

The present invention further provides a gas sensor comprising an inorganic powder whose weight loss caused by heating from room temperature to 700° C. when subjected to differential thermal analysis is not greater than 0.5%. When the weight loss of the inorganic powder measured at 700° C. is not greater than 0.5%, grains of the inorganic powder do not grow even in a working environment of 600° C. or higher, so that the gas sensor can maintain sufficient gastightness even in such a high temperature working environment.

The present invention still further provides a gas sensor comprising an inorganic powder whose specific surface area changes 19% or less (absolute value) during heat treatment performed at 700° C. for 24 hours. Hereinafter, the absolute value of a change in specific surface area is also called the "rate of change in specific surface area." When the rate of change in specific surface area is not greater than 19%, it is considered that grains of the inorganic powder do not grow even in a working environment of 600° C. or higher. Thus, the gas sensor can maintain sufficient gastightness.

Preferably, the inorganic powder is insulative and, in particular, contains $SiO_2$ and $MgO$ such that the total weight of $SiO_2$ and $MgO$ accounts for not less than 98 wt % of the weight of the inorganic powder. By using the inorganic powder, the gas sensor can favorably maintain gastightness. Alternatively, the inorganic powder contains $SiO_2$ and $Al_2O_3$ such that the total weight of $SiO_2$ and $Al_2O_3$ accounts for not less than 98 wt % of the weight of the inorganic powder. These inorganic powders are inexpensive and exhibit excellent compressibility so as to impart a hermetically sealed condition to the gas sensor.

Since the above-mentioned inorganic powders contain substantially no water glass, in general, it is difficult to obtain secondary particles thereof having a particle size convenient for compacting into a ring. Therefore, it is preferred to pulverize material stone of talc (i.e., raw talc from a mine) into particles having a particle size convenient for compacting into a ring, and to compact the particles into a ring. In the case where particles formed directly into a ring shape are produced from a material stone of talc by pulverization, pulverization is preferably performed such that the resultant particles have a particle size of 400 μm to 600 μm, because particles having a particle size of 400 μm to 600 μm flow smoothly into a die and exhibit good formability.

Further, in the case in which the inorganic powder as described above is charged into a gap between the metallic shell and the element, a portion of the metallic shell is caulked so as to compress the inorganic powder, whereby the gap between the metallic shell and the element can be properly filled with the inorganic powder, and can be sealed hermetically.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DESCRIPTION OF THE PREFERRED EMBODIMENTS

Embodiments of the present invention will next be described with reference to the drawings. However, the present invention should not be construed as being limited thereto.

Figure 1:
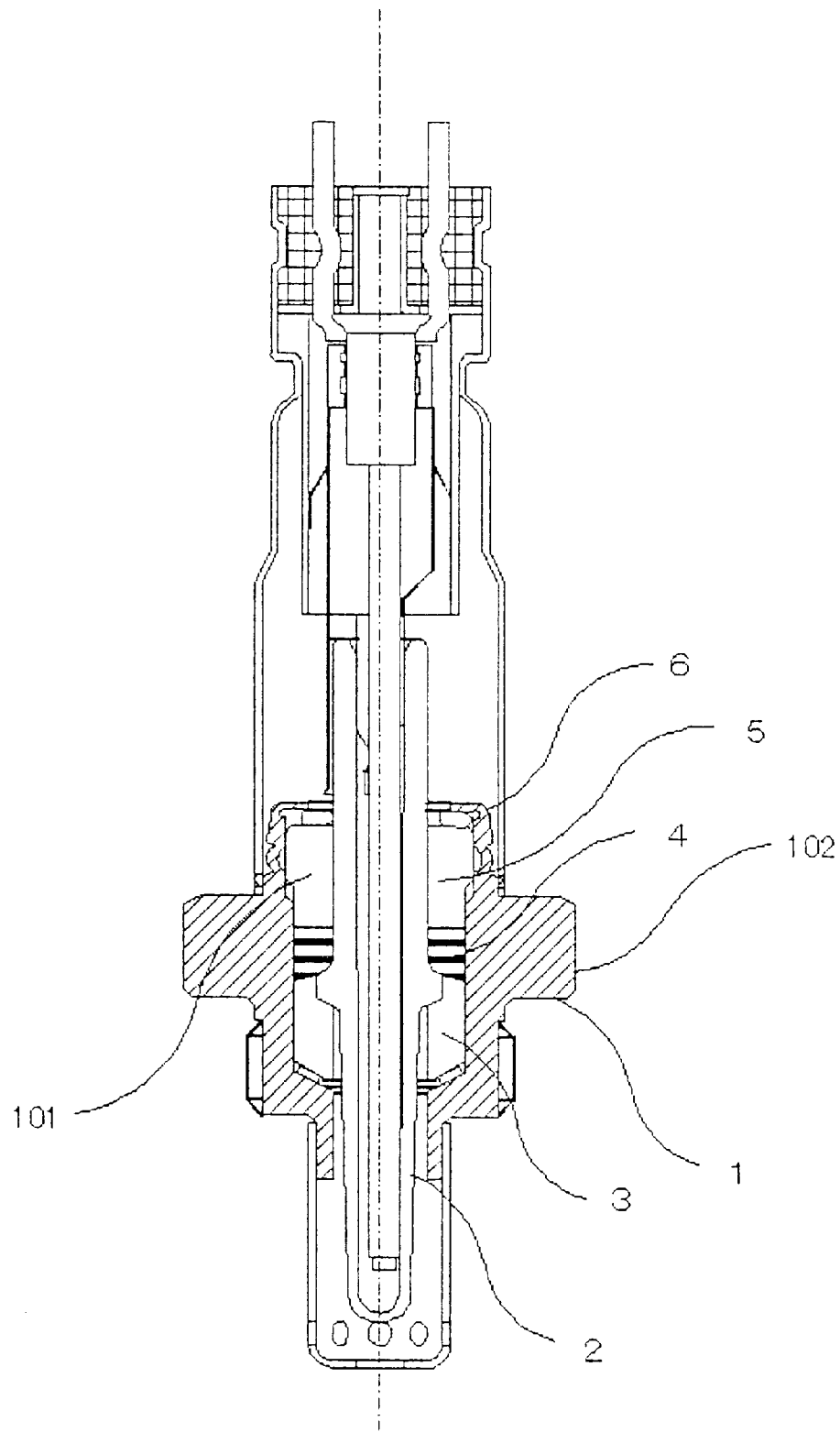
FIG. 1 is a sectional view showing a gas sensor according to an embodiment of the present invention.

FIG. 1 shows a gas sensor according to a first embodiment of the present invention. The gas sensor is used for measuring the concentration of oxygen contained in a gas to be measured. The gas sensor includes a sensing element 2 and a metallic shell 1 having an internal space 101 extending axially therethrough for accommodating the element 2. A holder 3, an inorganic powder 4, a sleeve 5, and a packing 6 are disposed in ascending order on top of one another in a gap between the element 2 and the metallic shell 1. An upper portion of the metallic shell 1 is caulked to thereby compress the inorganic powder 4 from above via the packing 6 and the sleeve 5. Caulking is performed under a caulking load of 25 KN applied for about 1 second.

EXAMPLES

Various inorganic powders as shown in Table 1 were prepared and subjected to differential thermal analysis. Table 1 shows the results of the analysis and the results of a gastightness test conducted after subjecting to a 600-hour endurance test at 700° C.

TABLE 1

| No. | Material | DTA Peak (up to 700° C.) | Weight Loss (wt %) | Gastight-ness After Endurance Test |
|---|---|---|---|---|
| 1 | HAICHENG talc (100 wt %) | Absent | 0.4 | Good |
| 2 | HAICHENG talc (100 wt %) + castor oil (2 wt %) | Present | 2.8 | No Good |
| 3 | HAICHENG talc (100 wt %) + water glass (4 wt %) + phenol (3 wt %) | Present | 2.6 | No Good |
| 4 | HAICHENG talc (100 wt %) + water glass (4 wt %) + water (3 wt %) | Present | 1.6 | No Good |

Figure 2:
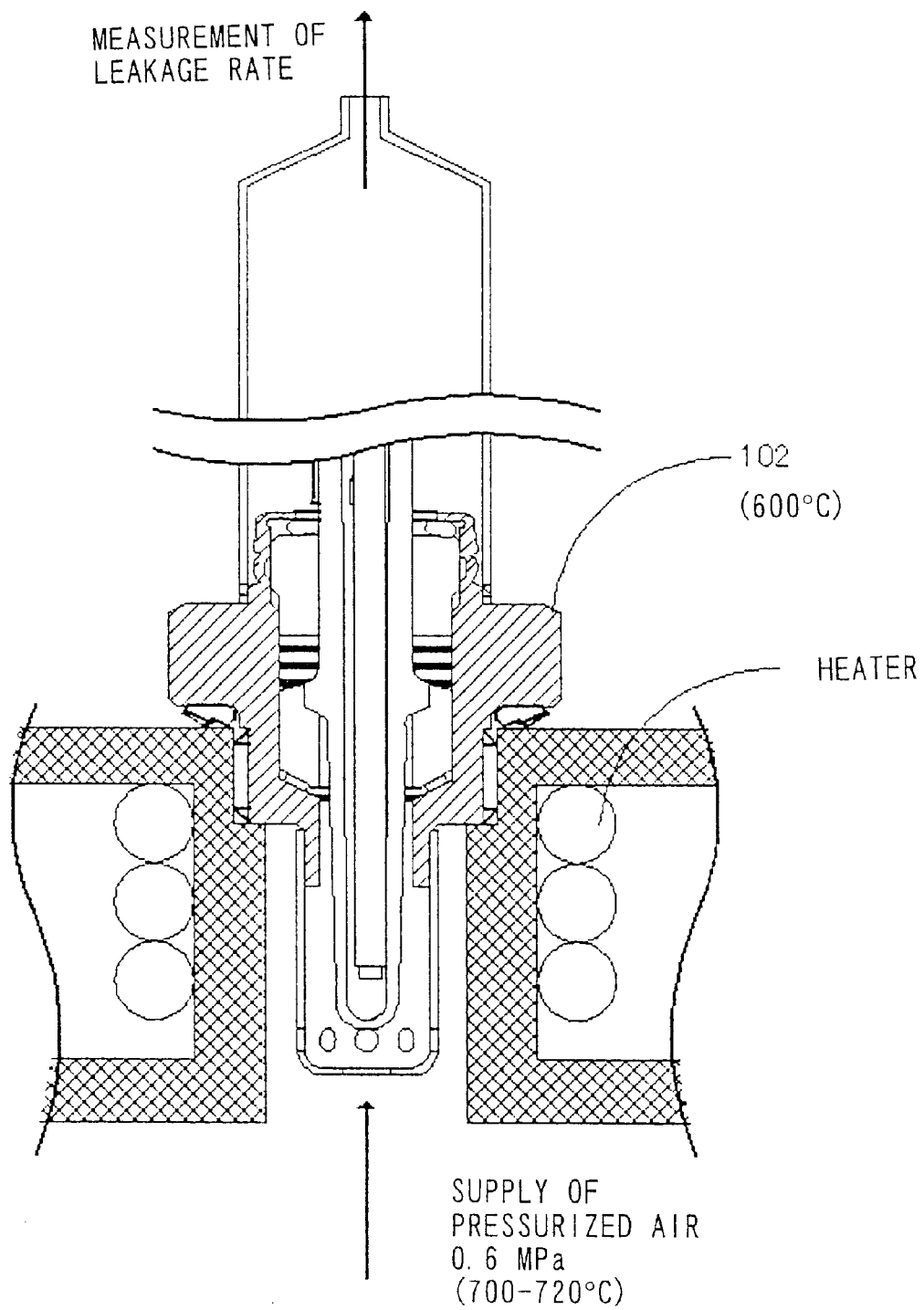
FIG. 2 is a sectional view showing a jig for testing gastightness of a gas sensor.

The differential thermal analysis was conducted on each of the inorganic powders (30 mg) using a differential thermal analyzer TG8101D (product of RIGAKU International Co., Ltd.). The analysis was conducted in the atmosphere with the temperature increasing at a rate of 10° C./min. While the temperature was varied from the room temperature to 1000° C., heat generation amount and percentage weight loss were measured. A percentage weight loss was calculated on the basis of a weight loss of each sample measured at 700° C. while the weight of the sample at room temperature was taken as 1. A gastightness test was conducted in the following manner. Gas sensors were assembled using the above-described corresponding inorganic powders. Each of the gas sensors was attached to a test unit shown in FIG. 2, and heated by means of a heater such that the temperature measured at a hexagonal portion 102 of the metallic shell of the gas sensor reached 600° C. Air heated to about 700° C. to 720° C. was applied at a positive pressure of 0.6 MPa to the gas sensor from the tip end side thereof. The flow rate of air leaking from the opposite side of the gas sensor was measured. Then, the gas sensor was subjected to a 600-hour endurance test while being heated such that the temperature of the inorganic powder portion thereof reached 700° C. Subsequently, the gas sensor was again attached to the test unit of FIG. 2 and was evaluated for the flow rate of leakage air under the same conditions as those employed in the initial measurement. Thus, the change in flow rate of leakage air before and after the endurance test was determined.

As seen from Table 1, in the case of a gas sensor using an inorganic powder which does not have an exothermic peak within a temperature range up to 700° C. when subjected to differential thermal analysis, the amount of leakage air did not change even after the endurance test, and good gastightness is maintained. Further, good gastightness is maintained in the case of a gas sensor using an inorganic powder whose weight loss measured at 700° C. is not greater than 0.5%.

The inorganic powders shown in Table 1 were subjected to a 24-hour endurance test which was conducted at 700° C. in the atmosphere. Subsequently, the inorganic powders were each measured for a change in specific surface area before and after the endurance test. The results are shown in Table 2.

TABLE 2

| | | Specific Surface Area (m²/cc) | | |
|---|---|---|---|---|
| No. | Material | Before Endurance Test | After Endurance Test | Absolute Value of Rate of Change |
| 1 | HAICHENG talc (100 wt %) | 0.64 | 0.63 | 1.6 |
| 2 | HAICHENG talc (100 wt %) + castor oil (2 wt %) | 0.55 | 0.66 | 20 |
| 3 | HAICHENG talc (100 wt %) + water glass (4 wt %) + phenol (3 wt %) | 0.71 | 0.57 | 20 |
| 4 | HAICHENG talc (100 wt %) + water glass (4 wt %) + water (3 wt %) | 0.61 | 0.36 | 41 |

As seen from Tables 1 and 2, gas sensors exhibiting a rate of change in specific surface area of not less than 20% exhibit impaired gastightness. Thus, the rate of change in specific surface area of an inorganic powder as determined by measuring the specific surface area before and after the 700° C. × 24-hour endurance test is preferably not greater than 19%.

The above-mentioned HAICHENG talc (product of KCM Co., Ltd.) is a mineral which is produced in the HAICHENG region, China and contains a predominant amount of $SiO_2$ and MgO. The total weight of $SiO_2$ and MgO accounts for not less than 98% of the weight of HAICHENG talc. An inorganic powder composed of $SiO_2$ and $Al_2O_3$ is also acceptable. Primary particles of these inorganic powders have a foliaceous shape or a squamiform shape and thus exhibit elasticity when compressed. Such "primary" particles are particles which have not been subjected to an applied pressure, and which may be deformed upon application of pressure or in a compaction process. Therefore, these inorganic powders are particularly useful for sealing a gas sensor.

Figure 3:
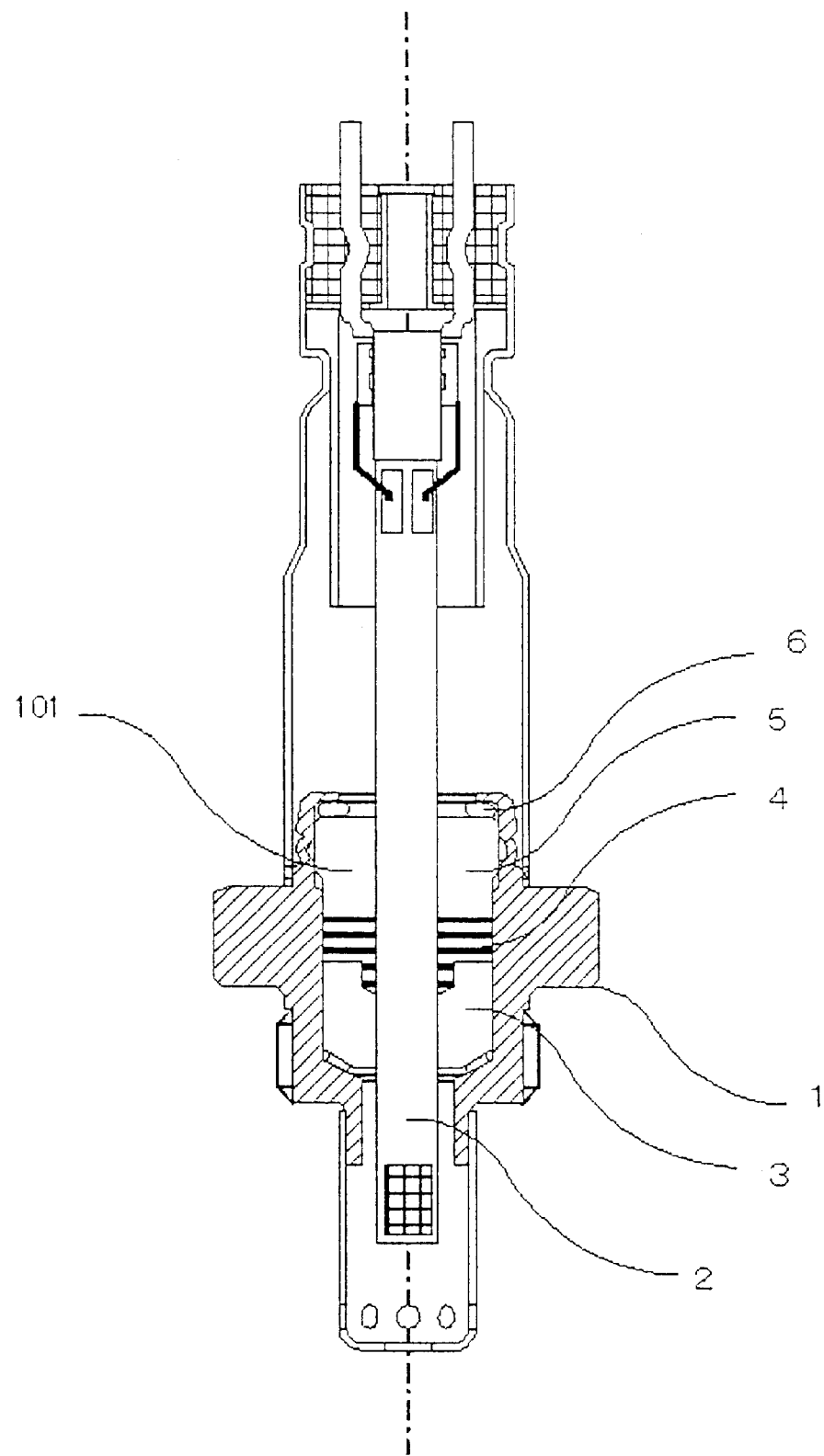
FIG. 3 is a sectional view showing a gas sensor according to another embodiment of the present invention.

The present invention is not limited to the above-described embodiments. For example, the present invention is applicable to a gas sensor employing a strip-shaped element as shown in FIG. 3. In the case of a gas sensor employing a strip-shaped element as disclosed in Japanese Patent Application Laid-Open (kokai) No. 9-127047, a ceramic holder which accommodates the element is accommodated in a metallic shell. Therefore, an inorganic powder for establishing gastightness is not filled into all gaps present between the element and the metallic shell but is filled only into the gap between the ceramic holder and the metallic shell. The present invention is even applicable to the disclosed gas sensor, whereby good gastightness can be maintained even at high temperature.

Clearly, numerous modifications and variations of the present invention are possible in light of the above teachings. It is therefore to be understood that within the scope of the appended claims, the present invention may be practiced otherwise than as specifically described herein.

The application is based on Japanese Patent Application No. 2000-018317, filed Jan. 27, 2000, the disclosure of which is incorporated herein by reference in its entirety.

What is claimed is:

1. A gas sensor comprising:
   an element for measuring the concentration of a component gas contained in a gas to be measured;
   a metallic shell having an internal space extending axially therethrough for accommodating said element; and
   an inorganic powder filling at least a portion of a gap between said metallic shell and said element, said inorganic powder having a grain size of 400 μm to 600 μm prior to filling the gap between the metallic shell and the element;
   wherein said inorganic powder does not have an exothermic or endothermic peak within a temperature range up to 700°C. when subjected to differential thermal analysis.

2. The gas sensor according to claim 1, wherein said inorganic powder contains at least $SiO_2$ and MgO, and the total weight Of $SiO_2$ and MgO accounts for not less than 98 wt % of the weight of said inorganic powder.

3. The gas sensor according to claim 1, wherein said inorganic powder contains at least $SiO_2$ and $Al_2O_3$, and the total weight of $SiO_2$ and $Al_2O_3$ accounts for not less than 98 wt % of the weight of said inorganic powder.

4. The gas sensor according to claim 1, wherein primary particles of said inorganic powder have a foliaceous shape or a squamiform shape.

5. A gas sensor comprising:
   an element for measuring the concentration of a component gas contained in a gas to be measured;
   a metallic shell having an internal space extending axially therethrough for accommodating said element; and
   an inorganic powder filling at least a portion of a gap between said metallic shell and said element, said inorganic powder having a grain size of 400 μm to 600 μm prior to filling the gap between the metallic shell and the element;
   wherein a weight loss of said inorganic powder caused by heating from room temperature to 700°C. when subjected to differential thermal analysis is not greater than 0.5%.

6. The gas sensor according to claim 5, wherein said inorganic powder contains at least $SiO_2$ and MgO, and the total weight of $SiO_2$ and MgO accounts for not less than 98 wt % of the weight of said inorganic powder.

7. The gas sensor according to claim 5, wherein said inorganic powder contains at least $SiO_2$ and $Al_2O_3$, and the total weight of $SiO_2$ and $Al_2O_3$ accounts for not less than 98 wt % of the weight of said inorganic powder.

8. The gas sensor according to claim 5, wherein primary particles of said inorganic powder have a foliaceous shape or a squamiform shape.

9. A gas sensor comprising:
   an element for measuring the concentration of a component gas contained in a gas to be measured;
   a metallic shell having an internal space extending axially therethrough for accommodating said element; and
   an inorganic powder filling at least a portion of a gap between said metallic shell and said element, said inorganic powder having a grain size of 400 μm to 600 μm prior to filling the gap between the metallic shell and the element;
   wherein a change in specific surface area of said inorganic powder caused by heat treatment carried out at 700°C. for 24 hours is not greater than 19%.

10. The gas sensor according to claim 9, wherein said inorganic powder contains at least $SiO_2$ and MgO, and the total weight Of $SiO_2$ and MgO accounts for not less than 98 wt % of the weight of said inorganic powder.

11. The gas sensor according to claim 9, wherein said inorganic powder contains at least $SiO_2$ and $Al_2O_3$, and the total weight of $SiO_2$ and $Al_2O_3$ accounts for not less than 98 wt % of the weight of said inorganic powder.

12. The gas sensor according to claim 9, wherein primary particles of said inorganic powder have a foliaceous shape or a squamiform shape.

13. A method for manufacturing a gas sensor including an element for measuring the concentration of a component gas contained in a gas to be measured, a metallic shell having an internal space extending axially therethrough for accommodating said element, and an inorganic powder filling at least a portion of a gap between said metallic shell and said element, the method comprising the steps of:

producing an inorganic powder having a grain size of 400 $\mu$m to 600 $\mu$m by pulverizing a material stone of talc;

forming the inorganic powder into a ring;

inserting the ring into a gap between the element and the metallic shell; and applying pressure to the ring so as to fill the gap with the inorganic powder in a compressed state.

\* \* \* \* \*